US005502042A

United States Patent [19]

Gruskin et al.

[11] Patent Number: 5,502,042
[45] Date of Patent: Mar. 26, 1996

[54] METHODS AND COMPOSITIONS FOR TREATING WOUNDS

[75] Inventors: Elliott A. Gruskin, Killingworth; Ying Jiang, North Haven, both of Conn.

[73] Assignee: United States Surgical Corporation, Norwalk, Conn.

[21] Appl. No.: 278,778

[22] Filed: Jul. 22, 1994

[51] Int. Cl.$^6$ .............................. A01N 43/04; C07H 5/04
[52] U.S. Cl. .................. 514/59; 514/54; 536/55.1
[58] Field of Search .................. 514/59, 54; 536/55.1

[56] References Cited

U.S. PATENT DOCUMENTS

| | | | |
|---|---|---|---|
| 2,988,455 | 6/1961 | Rosenberg et al. | 106/169 |
| 3,042,667 | 7/1962 | Flodin et al. | 260/209 |
| 4,308,254 | 12/1981 | Tayot et al. | 424/124 |
| 4,339,360 | 7/1982 | Shimizu et al. | 524/28 |
| 4,370,476 | 1/1983 | Usher et al. | 536/113 |
| 4,591,638 | 5/1986 | Ahrgren et al. | 536/51 |
| 4,963,666 | 10/1990 | Mälson | 536/55.1 |
| 4,988,358 | 1/1991 | Eppley et al. | 623/16 |
| 5,092,883 | 3/1992 | Eppley et al. | 623/11 |
| 5,336,501 | 8/1994 | Czech et al. | 424/445 |

FOREIGN PATENT DOCUMENTS

| | | |
|---|---|---|
| 562862 | 9/1993 | European Pat. Off. . |
| 562864 | 9/1993 | European Pat. Off. . |
| 1013585 | 12/1965 | United Kingdom . |

OTHER PUBLICATIONS

CA 112:104811 1990.

*Primary Examiner*—Paul J. Killos

[57] ABSTRACT

Wound treatment compositions include an oxidized cross-linked polysaccharide which has a chemically induced charge. Preferred polysaccharides are cross-linked dextrans. A charge is preferably provided by diethylaminoethyl groups (DEAE groups) or carboxymethyl groups. The oxidized cross-linked polysaccharide can be applied as a powder directly to a wound site. Alternatively, the oxidized cross-linked polysaccharide can be combined with a delivery vehicle to form a liquid or paste to be applied to a wound site.

20 Claims, No Drawings

METHODS AND COMPOSITIONS FOR TREATING WOUNDS

BACKGROUND

1. Technical Field

This disclosure relates generally to methods and compositions for treating wounds. More particularly, wounds are treated with a biodegradable composition containing oxidized cross-linked dextran or dextran derivative having a charged induced thereon.

2. Background of Related Art

Dextran is a polysaccharide which is produced from sucrose by bacteria belonging to the genera Leuconostoc, Streptococcus and Lactobacillus, all of which belong to the family Lactobacillaceae. The majority of known dextrans are formed by strains of *Leuconostoc mesenteroides*. Dextran, in which 1–6 linkages predominate, may be represented as follows:

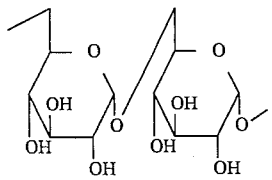

Dextran has been employed in the treatment of wounds. In particular, an insoluble hydrophilic cross-linked dextran polymer in powder form has been found to be especially useful for the debridement of wounds, i.e., the removal of foreign bodies, pus, exudates and irrevocably damaged and devitalized tissue from tissue wounds. This dextran polymer, which is formed by crosslinking dextran with epichlorohydrin, is applied to heavily exudating wounds, allowed to gel and then washed out. The crosslinked dextran, commercially known as DEBRISAN®, absorbs the exudates, including the components that tend to impede tissue repair. Consequently, this composition promotes wound healing by retarding eschar formation and by keeping lesions soft and pliable.

Dextran which is crosslinked with epichlorohydrin is described in U.S. Pat. No. 3,042,667 and in British Patent No. 1,013,585 and commercially available under the tradename SEPHADEX from Pharmacia Corp., Piscataway, N.J. Epichlorohydrin ($CH_2OCHCH_2Cl$) reacts with the pendant hydroxyl groups on dextran to form ether bound bridges between dextran chains. These ether bonds are not susceptible to degradation at physiological pH. Thus, the resulting crosslinked dextran is not considered to be biodegradable, a factor which considerably limits the utility of such crosslinked dextran.

U.S. Pat. No. 4,963,666 describes a method for overcoming this deficiency by providing a crosslinked dextran material containing ester bound crosslinking bridges. Ester bonds are much more susceptible to hydrolytic degradation at physiological pH than are ether bonds. The method of obtaining these ester bonds involves reacting a carboxyl-containing polysaccharide, e.g., hyaluronic acid, pectin, xanthan, alginic acid or an anionic derivative of a neutral polysaccharide such as carboxymethyl dextran, with an epoxy-type activating reagent such as epichlorohydrin. The resulting crosslinked dextran forms a gel of controllable degradability which may be employed as a tissue anti-adhesion agent, a drug-release agent or a wound dressing.

U.S. Pat. No. 4,591,638 discloses that dextran can be crosslinked via ester bonds by reacting dextran with reactive derivatives of dicarboxylic acids, e.g., diacyl halides.

Oxidation of polysaccharides including dextran has been performed for various purposes. For example, U.S. Pat. No. 2,988,455 describes water resistant cross-linked polysaccharide compositions wherein polysaccharide film-forming gums are cross-linked polysaccharide compositions wherein polysaccharide film-forming gums are cross-linked in combination with dialdehyde or periodate oxidized polysaccharides useful in forming films, coatings and innocuous vehicles for fillers.

U.S. Pat. No. 4,370,476 relates to the preparation of Ferric hydroxide complexes of dextran carboxylic acids. U.S. Pat. No. 4,339,360 relates to the production of particles of an activated oxidized polysaccharide substance (e.g., Sephadex) coated with an inactive protective layer. U.S. Pat. No. 4,308,254 relates to a porous solid material for use in a chromatography column prepared by a method which includes the step of oxidizing a support which may secondarily cross-linked DEAE dextran.

SUMMARY

Wound treatment compositions include an oxidized cross-linked polysaccharide which has a chemically induced charge. Preferred polysaccharides are cross-linked dextrans. A charge is preferably provided by diethylaminoethyl groups (DEAE groups) or carboxymethyl groups. The oxidized cross-linked polysaccharide can be applied as a powder directly to a wound site. Alternatively, the oxidized cross-linked polysaccharide can be combined with a delivery vehicle to form a liquid or paste to be applied to a wound site.

DETAILED DESCRIPTION OF PREFERRED EMBODIMENTS

The present wound treatment composition includes an oxidized cross-linked polysaccharide having a chemically induced charge. Any cross-linked polysaccharide can be oxidized in accordance with this disclosure. The polysaccharide can be ionically or covalently cross-linked. Among the ionically cross-linked polysaccharides useful in preparing the present wound treatment compositions are alginic acid and pectic acid which complex with certain multivalent ions such as $Ca^{++}$ to provide ionic crosslinking. Among the covalently cross-linked polysaccharides, dextran and modified alginates are preferred for use in the present compositions. Cross-linked dextran is available under the tradename SEPHADEX from Pharmacia Corp., (Piscataway, N.J.). Modified, covalently cross-linked alginates can be prepared, for example, as described in PCT WO 93/09176.

A chemical charge should be chemically induced on the polysaccharide, preferably prior to oxidation. For example, a positive charge can be provided on the polysaccharide by reaction with diethylamino ethyl chloride. Cross-linked dextran having DEAE groups thereon is commercially available under the name DEAE-SEPHADEX from Pharmacia Corp., Piscataway, N.J. A polysaccharide having a negative charge can be achieved by providing carboxymethyl groups on the polysaccharide. Techniques for chemically including a charge on a polysaccharide are known. See, for example, U.S. Pat. Nos. 4,988,358 and 5,092,883 to Eppley et al., the disclosures of which are incorporated herein by reference.

The charged, cross-linked polysaccharide is oxidized to cleave a portion of the monosaccharide units to provide groups terminating in carboxyl groups. Specifically, for example, in a dextran, the group:

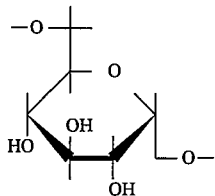

oxidizes to either of the following two structures, depending on the oxidizing agent employed and the oxidizing conditions:

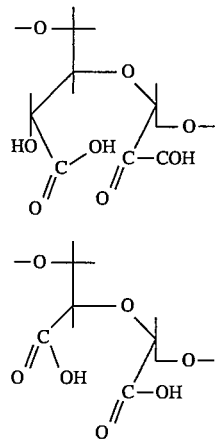

The linkages of structures I and II above are unstable under hydrolytical conditions and render the cross-linked polysaccharide biodegradable. The rate of biodegradation can be controlled by controlling the oxidation conditions to regulate the amount of monosaccharide units within the polysaccharides that are converted to structures I and/or II. Preferably, the oxidized, crosslinked polysaccharide will not completely lose its integrity until at least two days after application to a wound site.

The charged, cross-linked polysaccharide can be oxidized using any known technique. Periodate oxidation of the crosslinked polysaccharide is preferred. Periodate oxidation can be achieved by reacting the charged, cross-linked polysaccharide with periodic acid or a periodate salt such as sodium periodate. Although oxidation can be carried out at ambient temperatures, the temperature is preferably maintained between about 0° C. and 15° C., more preferably between about 2° C. and 10° C. The molarity of the periodic acid used in the oxidizing reaction preferably ranges from about 0.001M to about 1.0M, more preferably from about 0.01 to about 0.5M and most preferably from about 0.025 to about 0.10M. The reaction time for oxidation can vary depending on the molarity of the periodic acid and temperature of reaction. Normally, reaction times range from about 10 minutes to 24 hours. Preferably, reaction times of 0.5 to 5 hours are used.

In another embodiment, a two stage oxidation is carried out wherein periodate oxidation is followed by a second oxidation reaction. The oxidizing agents which can be used in the second oxidation reaction included bromine, sodium hypobromite, sodium bromite, chlorine, sodium hypochlorite and sodium chlorite, with sodium chlorite being preferred. Reaction conditions for the second oxidation can be the same as the conditions used for the periodate oxidation.

Once prepared, the oxidized cross-linked charged polysaccharide can be applied directly to a wound site. Thus, for example, where DEAE-Sephadex has been oxidized, the beads can be sprinkled directly onto a wound site by sprinkling from a shaker or other container having one or more openings in its lid.

In particularly useful embodiments the oxide cross-linked charged polysaccharide is mixed with a delivery vehicle to form a paste or fluid which can be applied to a wound. Any biocompatible fluid can be used as the delivery vehicle. Where the delivery vehicle is based on water, saline or some other polar fluid, it may be necessary to take steps to avoid premature hydrolysis of the modified polysaccharide. For example, the wound treatment can be provided as two separate components, namely the dry components (including the modified polysaccharide) in one container and the fluid component of the delivery vehicle in another container. The contents of the two containers are mixed shortly (preferably less than one hour) before application to the wound site. As another example, after mixing the modified polysaccharide and a polar delivery vehicle, the composition can be frozen to avoid premature hydrolysis. The wound treatment could be thawed shortly before application to a wound site.

Alternatively, the modified polysaccharide can be mixed with a delivery vehicle based on a non-polar fluid. Suitable non-polar fluids include, mineral oil, non-ionic surfactants, liquid low molecular weight poly(ethylene oxide) and liquid low molecular weight poly(propylene oxide).

The viscosity of the wound treatment will determine the method of its application. Thus, for example, low viscosity compositions can be sprayed or poured onto a wound site. Compositions having a paste-like or gel-like viscosity can be applied to a wound site via syringe or from a tube.

It may be desirable to package the wound treatment composition in a manner which prevents contact of the material with water. Known water impervious packages can be used. Additionally, the atmosphere within the package can be replaced with a dry, inert gas. Alternatively, a desiccant can be placed within the package.

The wound treatment composition can be sterilized using any technique which does not expose the composition to excessively hydrolyzing conditions. Accordingly, ethylene oxide or gamma radiation are preferred sterilization methods.

The wound treatment composition may optionally include additives such as fillers, colorants or viscosity modifiers. The wound treatment composition may also include a film-forming component if desired. Additionally, wound treatment composition may include one or more medico-surgically useful substances or therapeutic agent, e.g., those which accelerate or beneficially modify the healing process when particles are applied to a surgical repair site. The therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamicin sulfate, erythromycin or VX glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor bone morphogenetic protein, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system. It is also contemplated that the medico-surgically useful substance may enhance blood coagulation. Thrombin is one such substance.

The following non-limiting examples illustrate how the present novel compositions can be made and used.

EXAMPLE 1

Six grams of DEAE SEPHADEX A-25 (Pharmacia Corp., Piscataway, N.J.) and a 0.33M solution of periodic acid (prepared by placing 9.02 grams periodic acid in 120 ml distilled $H_2O$) are placed in a 250 ml 3-neck flask. The flask is placed in a recrystallizing dish maintained at 4° C. The mixture is reacted with stirring at 4° C. for about 2 days. The solution is then basified with 10N NaOH to a pH of about 11. Then the Sephadex mixture is suspended in 300 ml of distilled water for about 24 hours. The solution is then centrifuged and most of the water removed.

Three grams of the centrifuged Sephadex beads are suspended in 100 ml water and heated to 70° C. for 45 minutes. Then a solution of sodium chlorite (8.0 gm) and water (30 ml) are added to the suspension and stirred at 20° C. for about 24 hours. The pH is then adjusted to 4 by the addition of 1N HCl solution and the mixture is heated to 50° C. and maintained at 50° C. for one hour. Nitrogen is then passed through the flask until the solution turns colorless and the solution is suspended in 500 ml water for about 2 days. 1.6 grams of solid is obtained by centrifuging off water and then drying in vacuo overnight.

The degradability of the oxidized DEAE SEPHADEX beads is tested in vitro by placing about 0.75 grams of dried beads in a water bath maintained at 80° C. The beads are observed periodically through a microscope at 200X magnification. Initially, the beads swell upon contact with water. After 22 hours, more than 90 percent of the beads have degraded.

EXAMPLES 2–10

Into 9 different ml. Erlenmeyer flasks is placed 1 gram of DEAE-SEPHADEX A-25. Three solutions of periodic acid are prepared; namely, 0.165M, 0.0825M and 0.04125M solutions. 40 ml of each solution is poured into three flasks. The solutions are mixed and allowed to stand in the dark. One mixture from each solution is filtered at 1, 2 and 4 hours and the solid is washed thoroughly with water. The solid recovered is placed in saline buffer solution at 80° C. to determine in vitro degradation time. The results are summarized in the following Table:

| Example No. | $HIO_4$ | Reaction Time | Degradation Time |
| --- | --- | --- | --- |
| 2 | 0.165 M | 1 hr. | 60 min. |
| 3 | 0.0825 M | 1 hr. | 80 min. |
| 4 | 0.04125 M | 1 hr. | 100 min. |
| 5 | 0.165 M | 2 hrs. | 30 min. |
| 6 | 0.0825 M | 2 hrs. | 50 min. |
| 7 | 0.04125 M | 2 hrs. | 21 days |
| 8 | 0.0165 M | 4 hrs. | >20 min. |
| 9 | 0.0825 M | 4 hrs. | 20 min. |
| 10 | 0.04125 M | 4 hrs. | 12 days |

These experiments demonstrate the relationship between periodic acid concentration and reaction time on the degradation rate of the oxidized, crosslinked polysaccharide.

EXAMPLES 11–13

Three one gram samples of DEAE-SEPHADEX A-25 are oxidized by mixing with 40 ml. 0.061875M periodic acid for 1, 2 and 4 hours, respectively, at which time the solution is filtered and the solid material recovered is washed thoroughly with water. In vitro degradation time of approximately two days is determined for each sample by placing the solid in a saline buffer solution at 80° C.

EXAMPLE 14

A wound healing paste is formed by preparing a 20 mg/ml solution of the oxidized DEAE SEPHADEX of Example 7 in buffered saline and preparing a six percent solution of methylcellulose gel (3000 cps) in buffered saline. The two solutions are combined in a 50/50 mix to provide 100 ml of a paste having 10 mg/ml oxidized DEAE-SEPHADEX and 3% methylcellulose.

EXAMPLE 15

Adult female (235–250 g) Sprague-Dawley rats are anesthetized with sodium pentobarbital (43 mg/kg, IP) and their dorsal hair clipped and then depilated. Animals are then placed ventrally recumbent, and their dorsums are prepped with iodophor solution and 70% alcohol. Two paravertebral incisions are made on each animal's dorsum, beginning 2 cm caudal to the scapulae and separated by 3 cm. Incisions were created in a single motion through the panniculus carnosus using a #15 blade. After hemostasis is was achieved by blotting and/or pressure, 0.1 mls of either the formulation of Example 7 or a methyl cellulose control is applied by syringe to the incision. Then the wound edges are carefully approximated, using 3 strips of 0.5" wide microporous wound closure tape. Benzoin is applied to the intact skin about 5 mm from each wound edge to aid tape adherence. Both incisions are covered by a sterile gauze pad, and the animals are wrapped circumferentially with 3" wide cloth tape.

Ten days post surgery, the animals are euthenized and their bandages carefully removed. A template (6×7.5 cm) is placed on the dorsum so that the incisions are at its center. The template dimensions are outlined on the animal's skin with an indelible marker. The dorsal skin is then carefully removed from each animal, placed on a cutting board, repositioned to the original size of the template, and pinned. The wound closure tapes are carefully removed from each incision so that no distracting force is experienced by either incision. Three, 1.0 cm wide; skin strips are cut at once across the center of both incisions using a special multiple-blade cutting device. Each strip is then bisected to separate the two incisions. Thus, the 3 skin strips per wound and 6 strips per animal are produced.

The strength of each skin strip is determined using an Instron Universal Testing Machine (Model 1123), Instron Corp., Canton, Mass.). Each skin strip is mounted in pneumatic clamps (55 psi) so that the incision site is equidistant from each clamp. Then the clamps are distracted at a rate of 25 mm.min until the incision fails. The maximum force (g) endured by the strip prior to disruption is recorded as the healing strength of that strip. The strength values for the three strips from each given wound are averaged to yield one healing strength of the left incision are compared to that of the right incision, utilizing a Student's t-test for paired data. Wound tensile strength for wounds treated with the formulation of Example 7 was about 4.6 Newtons while wound tensile strength for wounds treated with the methyl cellulose control was 3.6 Newtons.

It will be understood that various modifications may be made to the embodiments disclosed herein. For example, the compositions in accordance with this disclosure can be blended with other biocompatible, bioabsorbable or non-bioabsorbable materials. Therefore, the above description should not be construed as limiting, but merely as exemplifications of preferred embodiments. Those skilled in art will envision other modifications within the scope and spirit of the claims appended hereto.

What is claimed is:

1. A composition comprising:
   a hydrolyzable wound treatment including an oxidized polysaccharide,
   wherein said polysaccharide is a cross-linked bead; and
   wherein said cross linked polysaccharide bead has a chemically induced charge thereon.

2. A composition as in claim 1 wherein the polysaccharide is dextran.

3. A composition as in claim 1 wherein the chemically induced charge is provided by diethylaminoethyl groups on the polysaccharide.

4. A composition as in claim 1 wherein the delivery vehicle comprises a non-polar fluid.

5. A composition as in claim 1 further comprising a therapeutically active substance.

6. A composition comprising a sterile wound treatment containing a hydrolyzable, cross-linked oxidized polysaccharide having a chemically induced charge.

7. A method of preparing a wound treatment composition comprising:
   providing a cross-linked polysaccharide having a charge chemically induced thereon; and
   oxidizing the cross-linked polysaccharide.

8. A method as in claim 7 wherein the cross-linked polysaccharide is cross-linked dextran.

9. A method as in claim 7 wherein the charge on the cross-linked polysaccharide is provided by diethylaminoethyl groups.

10. A method as in claim 7 wherein the oxidizing step comprises contacting the cross-linked polysaccharide with an oxidizing agent selected from the group consisting of periodic acid, periodic salts, sodium chlorite, sodium hypochlorite, sodium bromite and sodium hypobromite.

11. A method as in claim 7 wherein the oxidizing step comprises oxidizing the polysaccharide by reaction with periodate ion and further oxidizing the polysaccharide by reaction with sodium chlorite.

12. A method of treating a wound in a mammal comprising: applying a sterile wound treatment composition to a wound site, the wound treatment composition including and oxidized, cross-linked polysaccharide having a charge chemically induced thereon.

13. A method as in claim 12 wherein the wound treatment composition is a powder.

14. A method as in claim 12 wherein the wound treatment composition also includes a delivery vehicle.

15. A method as in claim 14 wherein the wound treatment composition is a gel.

16. A method as in claim 12 wherein the cross-linked polysaccharide is a cross-linked dextran.

17. A method as in claim 12 wherein the chemically induced change is provided by diethylaminoethyl groups on the polysaccharide.

18. A wound treatment composition comprising a cross-linked dextran wherein at least a portion of the monosaccharide units have been oxidized to a group having the following formula:

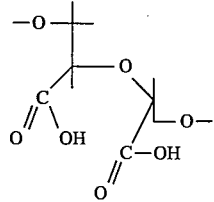

19. A wound treatment composition as in claim 18 wherein the cross-linked dextran has a charge chemically induced thereon.

20. A wound treatment composition as in claim 19 wherein the chemical charge is provided by DEAE groups on the cross-linked dextran.

* * * * *